(12) United States Patent
Berube et al.

(10) Patent No.: US 6,325,796 B1
(45) Date of Patent: Dec. 4, 2001

(54) MICROWAVE ABLATION INSTRUMENT WITH INSERTION PROBE

(75) Inventors: Dany Berube; M. Elizabeth Bush, both of Fremont, CA (US)

(73) Assignee: AFx, Inc., Fremont, CA (US)

( * ) Notice: Subject to any disclaimer, the term of this patent is extended or adjusted under 35 U.S.C. 154(b) by 0 days.

(21) Appl. No.: 09/305,143

(22) Filed: May 4, 1999

(Under 37 CFR 1.47)

(51) Int. Cl.$^7$ .................................................. A61B 18/18
(52) U.S. Cl. ............................ 606/33; 606/41; 607/101; 607/156
(58) Field of Search ............................ 606/32–35, 37–41; 607/99–101, 115, 116, 154, 156

(56) References Cited

U.S. PATENT DOCUMENTS

| | | | |
|---|---|---|---|
| 4,312,364 | * | 1/1982 | Convert et al. ........................ 607/156 |
| 4,448,198 | * | 5/1984 | Turner ..................................... 607/99 |
| 4,494,539 | | 1/1985 | Zenitani et al. . |
| 4,800,899 | * | 1/1989 | Elliott .................................... 607/156 |
| 5,507,743 | * | 4/1996 | Edwards et al. ........................ 606/41 |
| 5,737,384 | * | 4/1998 | Fenn ...................................... 607/101 |

OTHER PUBLICATIONS

Sato et al., *Two Long–term Survivors After Microwave Coagulation Therapy for Hepatocellular Carcinoma: A Case Report*, Hepatogastroenterology, Jul. 1996; 43 (10): 1035–1039 (Abstract).

Sato et al., "Microwave Coagulation Therapy For Hepatocellular Carcinoma", Gastroenterology, May 1996; 110(5):1507–1514. (Abstract)

Murakami et al., *Treatment of Hepatocellular Carcinoma: Value of Percutaneous Microwave Coagulation*, AJR AM J Roentgenol, May 1995; 164(5):1159–1164 (Abstract).

Labonte et al., "Monopole Antennas for Microwave Catheter Ablation", IEEE Trans. On Microwave Theory and Tech., 44, No. 10, 1832–1840 (1996).

* cited by examiner

*Primary Examiner*—Michael Peffley
(74) *Attorney, Agent, or Firm*—Beyer Weaver & Thomas

(57) ABSTRACT

A microwave ablation assembly and method including a relatively thin, elongated probe (21) having a proximal access end (22) and an opposite distal penetration end (23) adapted to penetrate into bio-tissue (25). The probe (21) defines an insert passage (26) extending therethrough from the access end (22) to the penetration end (23) thereof. An ablation catheter includes a coaxial transmission line (28) with an antenna device (30) coupled to a distal end of the transmission line (28) for generating an electric field sufficiently strong to cause tissue ablation. The coaxial transmission line (28) includes an inner conductor (31) and an outer conductor (32) separated by a dielectric material medium (33). A proximal end of the transmission line (28) is coupled to a microwave energy source. The antenna device (30) and the transmission line (28) each have a transverse cross-sectional dimension adapted for sliding receipt through the insert passage (26) while the elongated probe (21) is positioned in the bio-tissue (25). Such sliding advancement continues until the antenna device (30) is moved to a position beyond the penetration end (23) and further into direct contact with the bio-tissue (25).

41 Claims, 5 Drawing Sheets

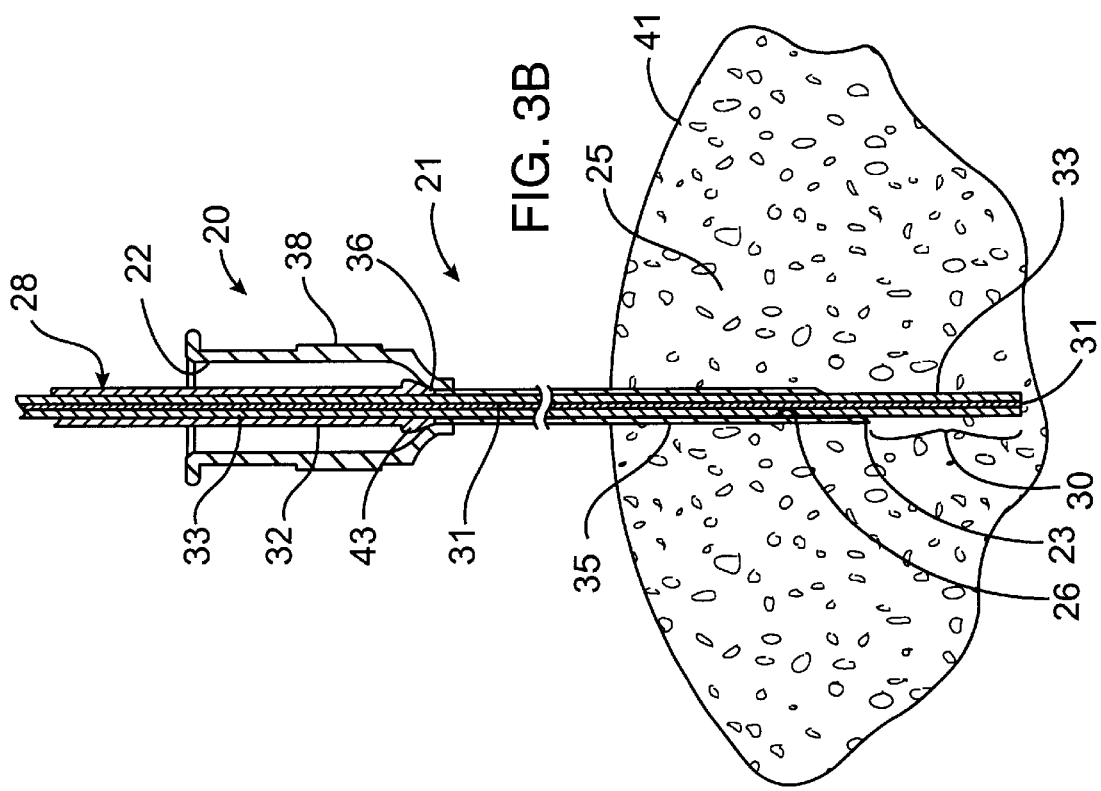
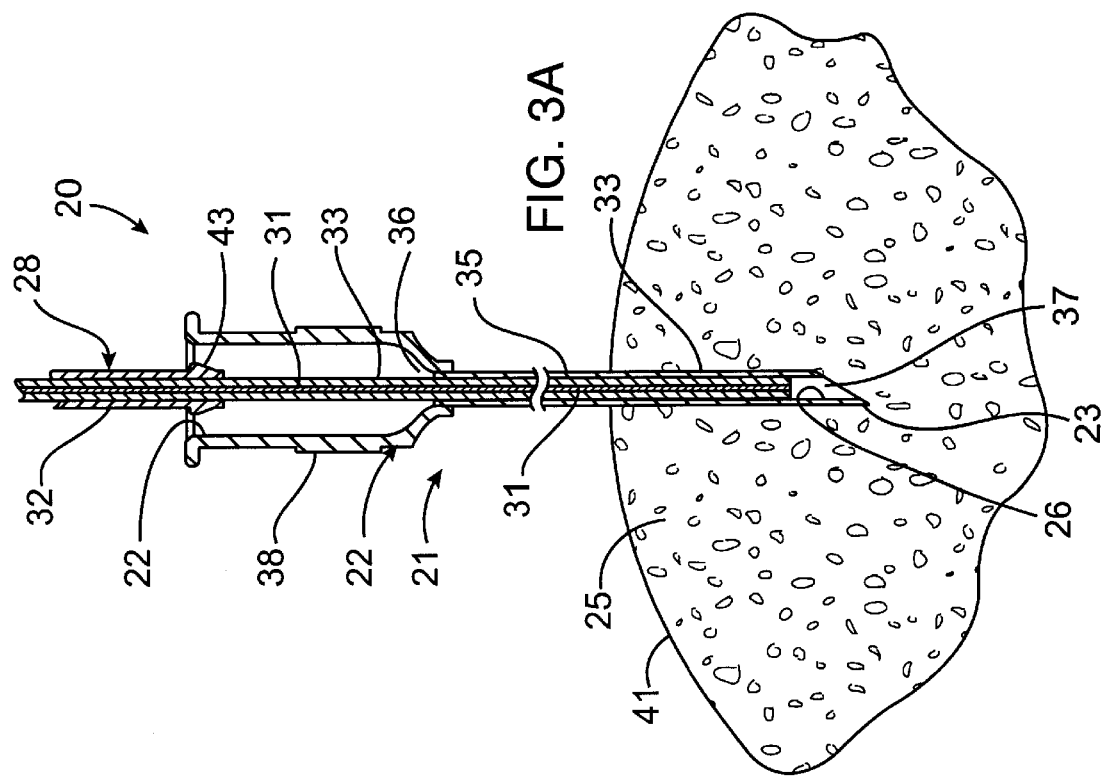

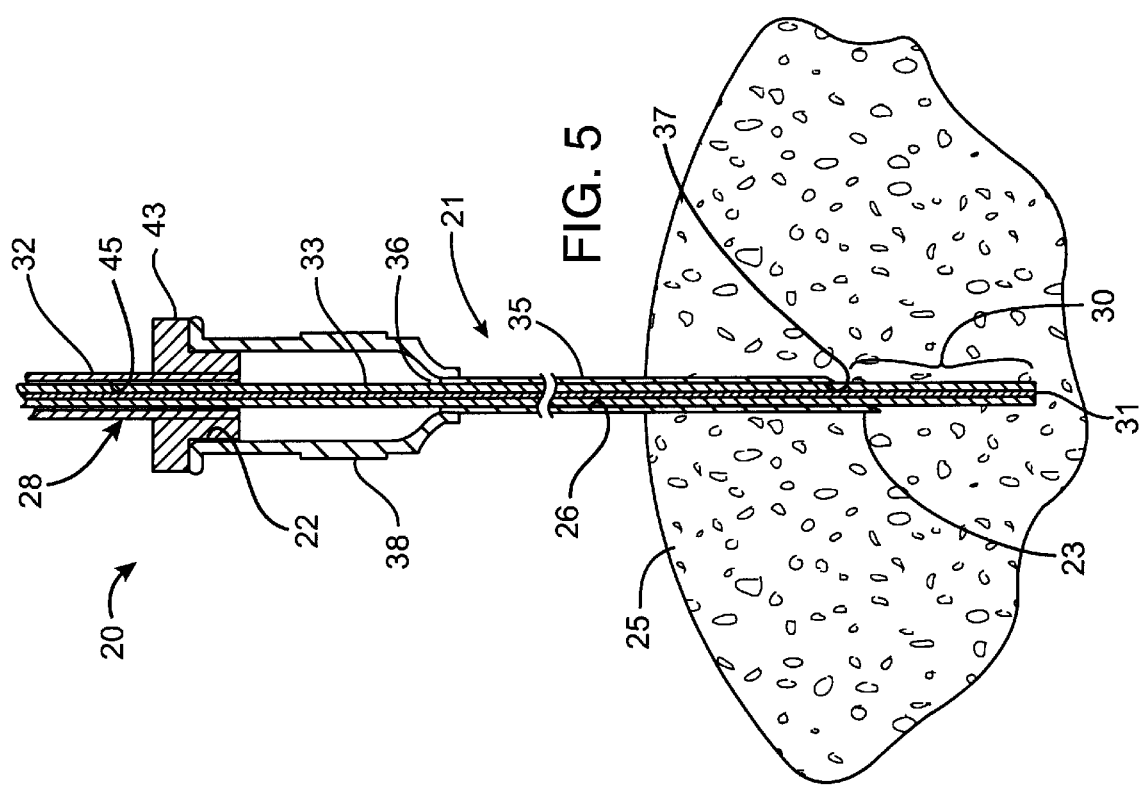
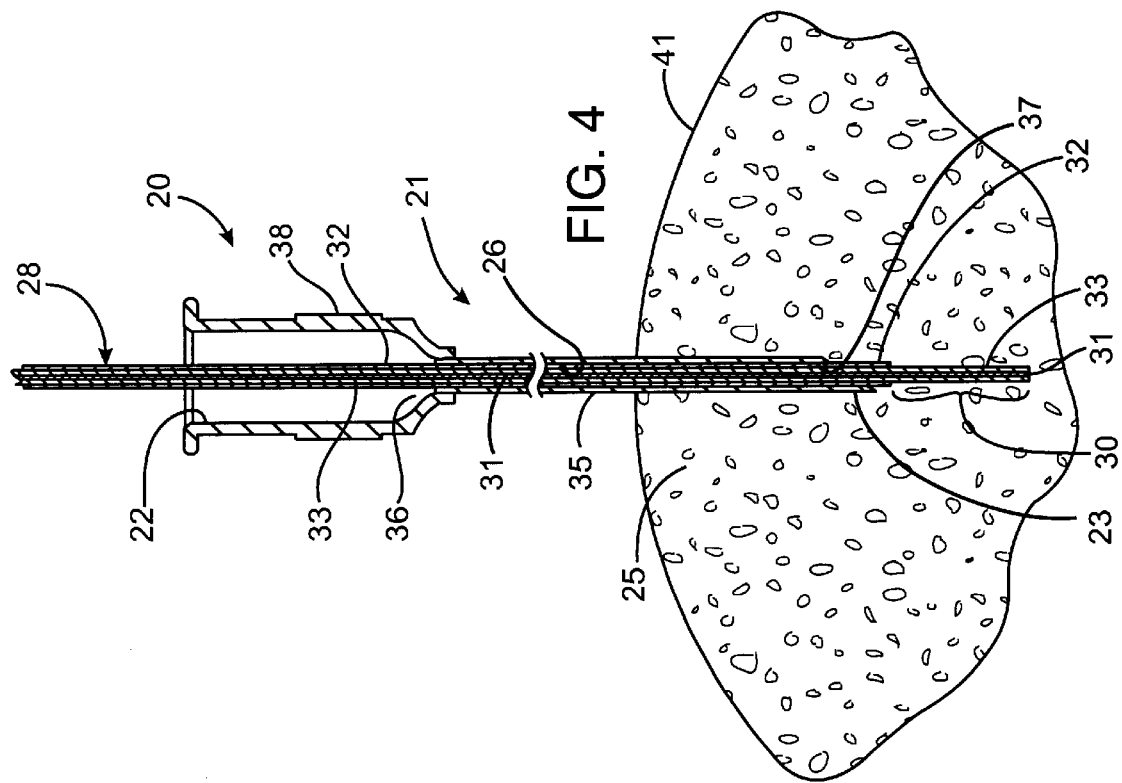

MICROWAVE ABLATION INSTRUMENT WITH INSERTION PROBE

BACKGROUND OF THE INVENTION

1. Field of Invention

The present invention relates, generally, to ablation instrument systems that use electromagnetic energy in the microwave frequencies to ablate internal bodily tissues, and, more particularly, to antenna arrangements and instrument construction techniques that direct the microwave energy in selected directions that are relatively closely contained along the antenna.

2. Description of the Prior Art

Hepatocellular carcinoma (HCC) is one of the most common liver malignancies in the world. Both in Asia and in the West, most HCC tumors emerge in patients with cirrhosis of the liver. In Japan, for example, liver cancer is the third most common cause of cancer death in men after gastric and cancers.

Yearly incidence of HCC in cirrhotic patients reaches 3–5%, and HCC is recognized as being part of the natural history of cirrhosis. In the past few years, owing to the careful follow-up of cirrhotic patients with ultrasonography (US) and serum alpha-fetoprotein assays, an increasing number of HCC lesions have been diagnosed in a preclinical stage. Although early detection of the tumors resulted in increased resectability rate, the number of patients with HCC eligible for surgery has remained relatively low. This is due to the severity of the associated liver cirrhosis (which may unacceptably increase the surgical risk) and to the frequent multifocality of the tumor. The latter is a critical issue since small doughter nodules may accompany the main tumor and go undetected causing early postoperative intrahepatic recurrences.

For patients who are considered ineligible for surgery, several nonsurgical treatments are available, such as percutaneous ethanol injection (PEI), transcatheter arterial chemoembolization (TACE) or a combination of TACE and PEI. The prognosis for patients with unresectable hepatocellular carcinoma (HCC) tumors is extremely poor, however. Even in the case of small nodular lesions detected by US screening, patients receiving no treatment showed a mean 3-year survival rate of only 12%. Among nonsurgical options, Percutaneous Ethanol Injection (PEI) can be considered the treatment of choice for patients with small (3 cm or less in diameter) HCC tumors. Studies in Japan and in Italy demonstrated the possibility of achieving complete alcohol-induced necrosis of such small lesions without adverse effects on the noncancerous liver parenchyma. Moreover, patients treated with PEI showed high long-term survival rates, comparable with those of patients submitted to surgical resection. The greatest drawback of PEI is represented by the difficulty to treat tumors larger than 3 cm. In these cases, alcohol diffusion is incomplete, being impeded by the texture of the tumor. As a result, residual viable neoplastic tissue can be found after treatment, particular along the periphery of the nodule or in portions isolated by septa.

Transcatheter Arterial Chemoembolization (TACE), most frequently performed by intraarterially injecting an infusion of antineoplastic agents mixed with iodized oil (Lipidol), has been extensively used in the treatment of large HCC tumors. However, although massive tumor necrosis can be demonstrated in most cases, a complete necrosis of the tumor has rarely been achieved with TACE, since residual tumor can be found in a noneligible number of the treated lesions. Indeed, TACE was found mostly effective in nodules less than 4 cm in diameter, with a thick tumor capsule.

Even if PEI or TACE can be effective for small tumors, there are still some patients with HCC who are not good candidates for resection, PEI or TACE because of poor hepatic reserve, poor vascularity, or the large size of the HCC. In these instances, microwave coagulonecrotic therapy may be employed as an alternative, the efficacy of which has been shown in several studies. Sato M. et al., *Two Long-Term Survivors After Microwave Coagulation Therapy For Hepatocellular Carcinoma: A Case Report*, PEPATOGASTROENTEROLOGY, July (1996) 43(10):1035–1039; Sato M. et al., *Microwave Coagulation Therapy For Hepatocellular Carcinom*, GASTROENTEROLOGY, May (1996) 110(5):1507–1514.

This coagulonecrotic technique consists of using microwave energy to the tumor cells to increase their temperature to around 55 to 60° C. Originally, a conventional microwave applicator was applied directly to the surface of the liver proximate the tumor cells. Such surface applications were necessary for these ablation catheters since the conventional microwave antennas were generally too diametrically large to be position inside the highly vascularized liver. Accordingly, the primary drawback of this surface application approach is that the tumor cells are not always within the penetration depth of the microwave energy.

In recent years, microwave needle antennas have been developed as a new option for destruction of unresectable HCCs. Using laparotomy, laparoscopy or through percutaneous methods, a relatively small diameter needle antenna may be punctured into the liver to ablate tumor cells from within the liver. This technique has been proven useful for penetrating this highly vascularized organ without causing excessive bleeding. The penetrations sites into the targeted tumor, however, must still be estimated.

Accordingly, there is a need for microwave coagulation therapy which can be more accurately applied within an organ.

SUMMARY OF THE INVENTION

The present invention provides a microwave ablation assembly including an elongated probe having a proximal access end and an opposite distal penetration end adapted to penetrate into bio-tissue. The probe further defines an insert passage extending therethrough from the access end to the penetration end thereof. A coaxial transmission line includes an inner conductor and an outer conductor separated by a dielectric material medium. A proximal end of the transmission line is coupled to a microwave energy source. The ablation assembly further includes an antenna device coupled to the transmission line for generating an electric field sufficiently strong to cause tissue ablation. The antenna device and the transmission line each have a transverse cross-sectional dimension adapted for sliding receipt through the insert passage while the elongated probe is positioned in the bio-tissue. Such sliding receipt occurs until the antenna device is advanced to a position beyond the penetration end and further into the bio-tissue.

Preferably, the antenna device is integrally formed by removing a portion of the outer conductor to expose a portion of the dielectric material medium. Thus, the transverse cross-sectional dimension of the antenna device is substantially equal or smaller than that of the transmission line. In one embodiment, the transverse cross-sectional dimension of dielectric material medium and that of the insert passage cooperate to prevent the outer conductor from extending through the insert passage. In this arrangement, a distal end of the outer conductor is adapted to electrically couple to the elongated probe proximate the access end of the elongated probe such that the probe functions as a shield for the transmission line.

In another arrangement, the outer conductor is provided by a conductive sleeve which is electrically coupled to the elongated probe prior. The dielectric material medium and the inner conductor are adapted for sliding receipt in the conductive sleeve and the insert passage of the probe as a unit to advance and retract the antenna device.

In still another embodiment, a microwave ablation assembly is provided for insertion through an insert passage of an elongated metallic biopsy needle having a penetration end adapted to penetrate into bio-tissue. The ablation assembly includes a coaxial transmission line including an inner conductor and an outer conductor separated by a dielectric material medium. An antenna device is coupled to the transmission line for generating an electric field sufficiently strong to cause tissue ablation. The antenna device and the transmission line each having a transverse cross-sectional dimension adapted for sliding receipt through the insert passage of the biopsy needle while the needle is positioned in the bio-tissue. The antenna device is further adapted to be advanced and positioned beyond the distal insert opening into the passage and further into the bio-tissue.

In another aspect of the present invention, a method for ablating bio-tissue is provided including: introducing an elongated probe into the bio-tissue to a predetermined depth, wherein the probe defines a passage extending therethrough from a proximal access end to an opposite distal end thereof. The method further includes introducing into the passage an elongated microwave ablation device having a distal antenna coupled to a transmission line which in turn is coupled to a microwave energy source at a proximal end thereof, and positioning the distal antenna at least at the probe distal end. Finally, the method includes generating an electric field at the distal antenna which is sufficiently strong to cause ablation of the bio-tissue within the electric field.

In one embodiment, the introducing an elongated probe includes piercing the opposite distal end thereof into the bio-tissue percutaneously. Moreover, the elongated probe is preferably provided by a biopsy needle, and the method further includes, after the piercing and before the introducing into the passage, removing a specimen of bio-tissue through the biopsy needle.

To form the antenna device in one configuration, the method of the present invention further includes removing a portion of the outer conductor proximate a distal end of the transmission line to expose a portion of the dielectric material medium to form the antenna device.

In yet another configuration, the method includes electrically connecting the outer conductor to the metallic biopsy needle. This causes the metallic needle to function as a portion of the transmission line and antenna device. This electrical connection may be formed by contacting the outer conductor with the biopsy needle during the advancing of the distal antenna into the insert passage.

The introducing into the passage includes inserting the distal antenna and the transmission line, as a single unit, through an access opening at the proximal access end of the probe and into the passage toward the distal end thereof. The positioning of the distal antenna further includes advancing the distal antenna through the passage to a position beyond the penetration end and further into the bio-tissue.

In still another embodiment, the electrically connecting includes precoupling a conductive sleeve of the outer conductor to the elongated probe prior to piercing, and the introducing into the passage further includes slideably inserting the inner conductor and the dielectric material medium as a unit into the conductive sleeve as a unit.

In another aspect of the present invention, a method of percutaneously ablating bio-tissue in a body cavity includes percutaneously piercing a penetration end of a biopsy needle into the bio-tissue to a predetermined depth from outside the body cavity, and inserting into the insert passage an elongated microwave ablation device having a distal antenna coupled to a transmission line which in turn is coupled to a microwave energy source at a proximal end thereof. The method further includes advancing the distal antenna through the insert passage to a position beyond the penetration end and further into the bio-tissue; and generating an electric field at the distal antenna which is sufficiently strong to cause ablation of the bio-tissue within the electric field.

The transmission line is preferably coaxial and is suitable for the transmission of microwave energy at frequencies in the range of about 400 to about 6000 megahertz, and includes an inner conductor and an outer conductor separated by a dielectric material medium therebetween. This method arrangement further includes removing a portion of the outer conductor proximate a distal end of the transmission line to expose a portion of the dielectric material medium to form the antenna device.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIGS. 3A and 3B is a sequence of enlarged side elevation view, in cross-section, of one embodiment of a microwave ablation instrument assembly of FIG. 2 being inserted and advanced through the biopsy needle.

FIG. 4 is an enlarged side elevation view, in cross-section, of the microwave ablation instrument assembly of FIG. 3, and illustrating electrical coupling between the outer connector of the instrument assembly and the conductive biopsy needle.

FIG. 5 is an enlarged side elevation view, in cross-section, of another embodiment of the microwave ablation instrument assembly of FIG. 2.

DETAILED DESCRIPTION OF THE INVENTION

Figure 1:
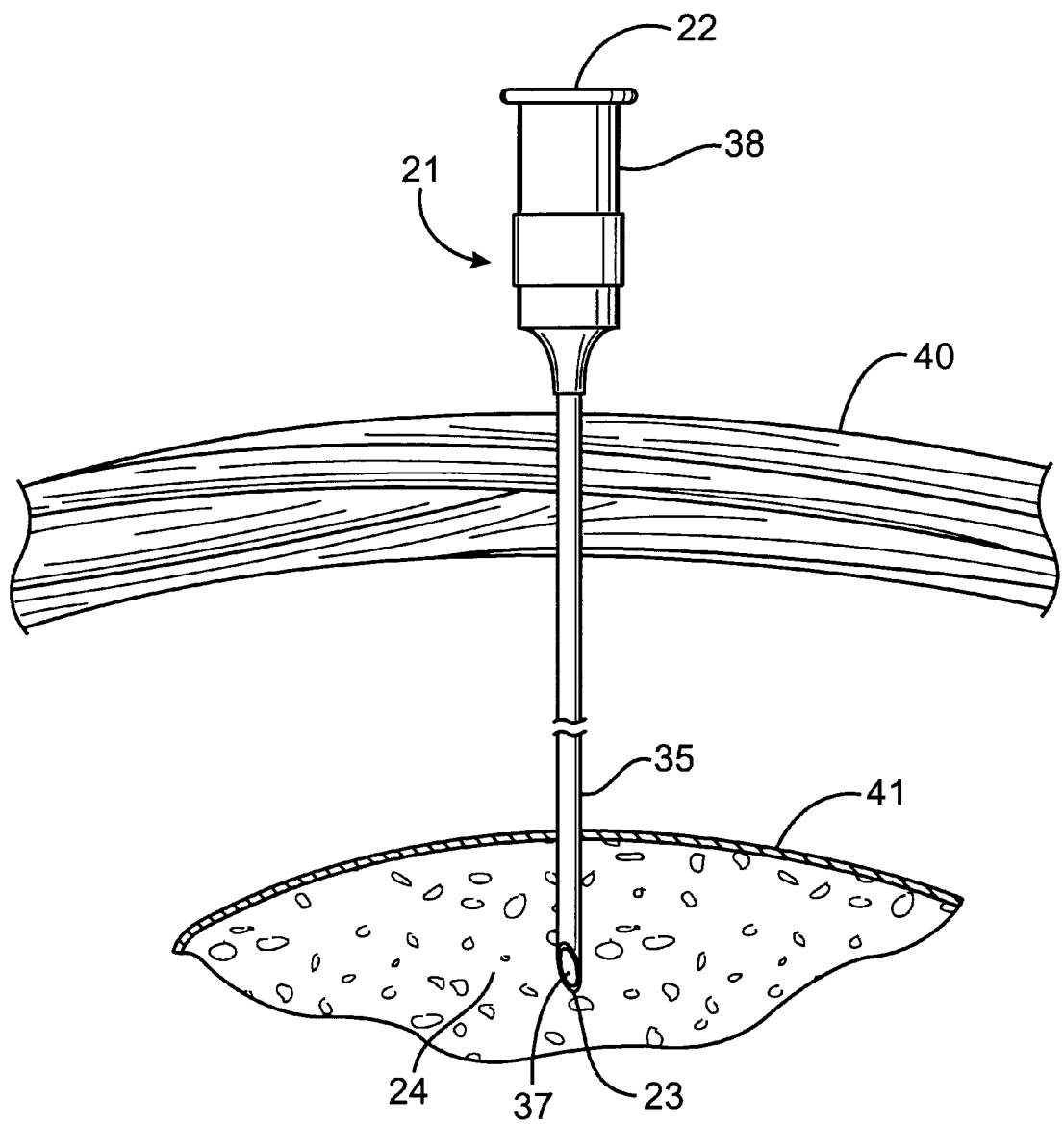
FIG. 1 is a diagrammatic side elevation view, in cross-section, of a biopsy needle percutaneously penetrating a body cavity.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various FIGURES.

Figure 2:
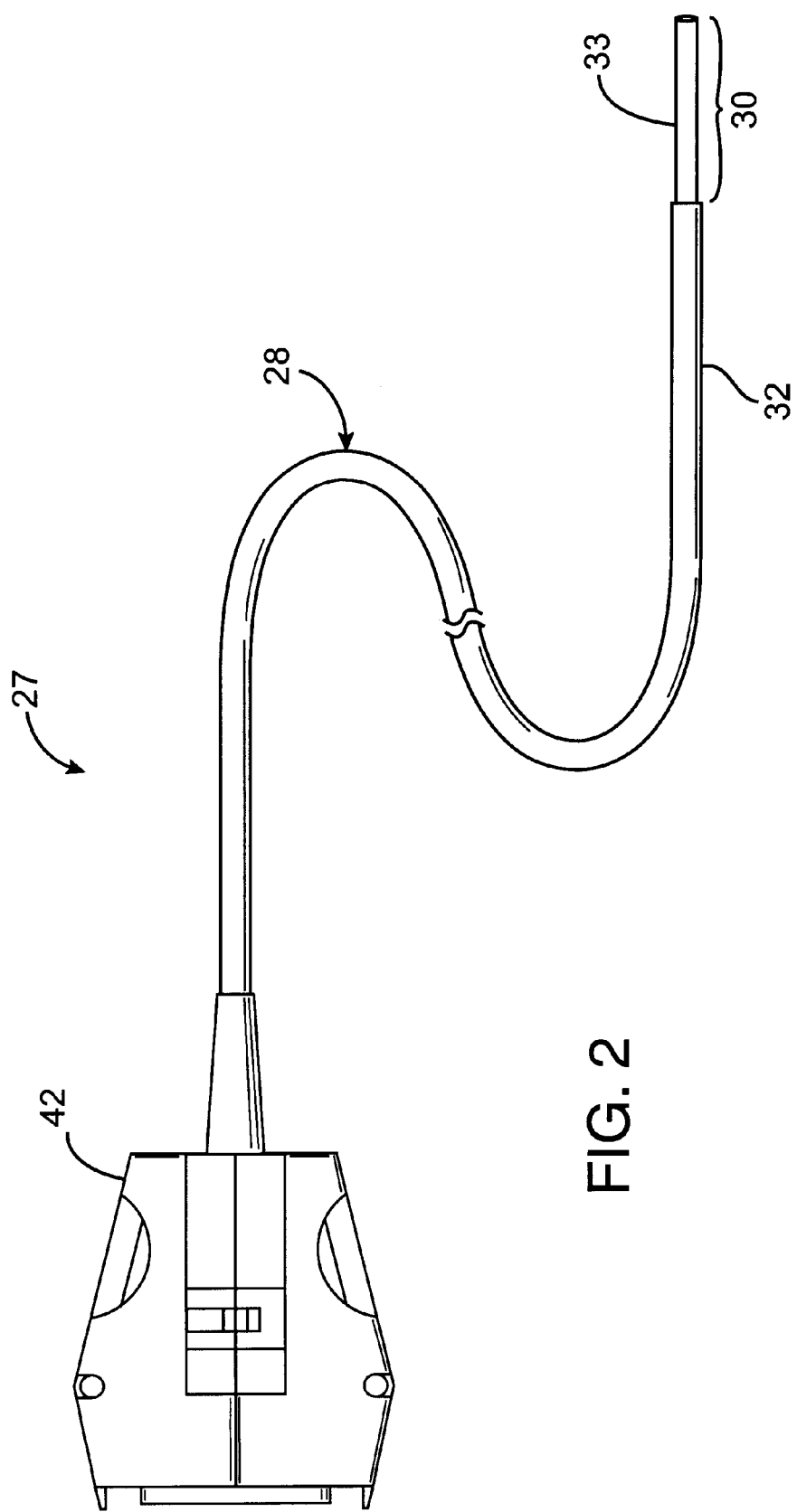
FIG. 2 is a top plan view of a microwave ablation instrument assembly constructed in accordance with the present invention.

Turning now to FIGS. 1–3, a microwave ablation assembly, generally designated 20, is provided including a relatively thin, elongated probe 21 having a proximal access end 22 and an opposite distal penetration end 23 adapted to penetrate into bio-tissue 25. The probe 21 further defines an insert passage 26 extending therethrough from the access end 22 to the penetration end 23 thereof. The ablation assembly 20 further includes an ablation catheter, generally designated 27, having a coaxial transmission line 28 with an antenna device 30 coupled to a distal end of the transmission line 28 for generating an electric field sufficiently strong to cause tissue ablation. The coaxial transmission line includes an inner conductor 31 and an outer conductor 32 separated by a dielectric material medium 33. A proximal end of the transmission line 28 is coupled to a microwave energy source (not shown). The antenna device 30 and the transmission line 28 each have a transverse cross-sectional dimension adapted for sliding receipt through the insert passage 26 while the elongated probe 21 is positioned in the bio-tissue 25. Such sliding advancement continues until the antenna device 30 is moved to a position beyond the penetration end 23 and further into direct contact with the bio-tissue 25.

Accordingly, a microwave ablation assembly is provided which utilizes a thin, elongated probe as a deployment mechanism to position the antenna of the microwave ablation catheter within the bio-tissue targeted for ablation. Once the probe is positioned, the antenna device and the transmission line are inserted through the passage of the probe as a unit until the antenna device contacts the targeted bio-tissue at the distal end of the probe. Subsequently, an electric field is emitted from the antenna device which is sufficiently strong to cause tissue ablation.

This arrangement is especially beneficial when the tumorous cells targeted for ablation are located in highly vascularized organs, such as the liver. For instance, the tubular probe may be employed to acquire biopsy specimens at selected sites of penetration. This assures that the microwave ablation antenna will be accurately positioned in the targeted ablation region. Moreover, the relatively small diameter antenna device and corresponding transmission line enable the use of a relatively small diameter probe to minimize the size of the puncture site.

In the preferred embodiment, the elongated probe 21 is provided by a metallic biopsy needle having an elongated needle shaft 35 adapted to percutaneously pierce through body tissue 25 at a distal penetration end 23. The insert passage 26 extends longitudinally through the needle shaft 35, and includes a proximal access opening 36 and an opposite distal penetration opening 37 at the distal penetration end 23 thereof. At the proximal end of the needle shaft 35 is a hollow connector member 38 which facilitates insertion of objects into the proximal access opening 36 of the insert passage 26. FIG. 1 best illustrates that the distal penetration end 23 is preferably in the form of a conventional beveled tipped needle or a beveled point chamfered needle which forms sharp cutting edge.

These biopsy needle shafts 35 are preferably thin walled stainless steel tubes having a wall thickness in the range of between about 0.010 inch to about 0.025 inch, and more preferably about 0.015 inch. The diameter of the insert passages 26 is preferably in the range of about 0.015 inch to about 0.060 inch, and more preferably about 0.035 inch. In accordance with the present invention, this relatively small diameter size is particularly suitable for use in highly vascularized organs, such as the liver, so as to minimize the puncture diameter and, thus, potential bleeding. It will be appreciated, of course, that the present invention may be utilized to ablate the bio-tissue of other organs or tissue as well. Typical of these biopsy needles is the Menghini Technique Aspirating Needle Set or the Klatskin Needle Set by POPPER®.

Using conventional viewing and positioning techniques, the penetration end 23 of the biopsy needle 21 may percutaneously positioned through the skin or bodycavity 40, and into the targeted organ 41 or other bio-tissue. Depending upon the depth of penetration, the bio-tissue 25 surrounding the needle shaft 35 may be employed to vertically and laterally support the biopsy needle 21 during specimen collection and tissue ablation. Once the distal penetration end 23 of the needle shaft 35 is placed at the proper selected depth, such as that shown in FIGS. 1 and 3, a specimen of bio-tissue may be collected using a suction syringe. Such specimen acquisition techniques, however, depend upon the particular type of biopsy probe employed.

Upon collection of the specimen, the bio-tissue may be analyzed to determine whether the distal penetration end 23 is properly positioned in or sufficiently proximate to the bio-tissue targeted for ablation. In this manner, the microwave ablation of tissues may be conducted with substantially more accuracy so that inadvertent and irreparable microwave ablation of the non-tumorous cells may be better controlled.

In accordance with the present invention, once the biopsy needle 21 is properly positioned and retained at the targeted penetration site, the antenna device 30 of the ablation catheter 27 may then be inserted through the connector member 38 and into the access opening 36 of the insert passage 26. As best view in FIG. 3A, the antenna device 30 and the associated transmission line 28 are advanced longitudinally through the passage 26 of the needle shaft 35 to the distal penetration end 23 thereof. Upon subsequent axial advancement, the antenna device 30 may be manipulated to extend though the penetration opening 37 of the insert passage for further penetration into the targeted bio-tissue 25 (FIG. 3B). Such advancement causes the antenna device 30 to be in direct contact with the targeted tissue for microwave ablation thereof.

Accordingly, the antenna device 30 and the transmission line 28 are preferably cooperatively structured to enable axial penetration of the bio-tissue by the antenna during advancement thereof past the distal penetration end 23 of the elongated needle 21. Thus, both the antenna device 30 and the transmission line 28 must be sufficiently axially and laterally rigid to enable axial penetrative manipulation of the transmission line 28 from the connector member side of the biopsy needle 21. Alternatively, as will be described in greater detail below, only selected portions of the transmission line need be laterally supported where necessary to facilitate axial advancement of the antenna into the bio-tissue. This is especially true when piercing tumor cells which are typically more resistant to penetration due to a thick tumor capsule.

Referring back to FIG. 2, the microwave ablation catheter 27 is illustrated having an elongated flexible transmission line 28. At a proximal end of the transmission line 28 is an electrical connector 42 adapted to electrically couple the antenna device 30 to the microwave energy source (not shown). At the distal end is the antenna device 30 which is adapted to generate microwaves in directions radially from the longitudinal axis thereof.

Briefly, the microwave energy source or power supply includes a microwave generator which may take any conventional form. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz may be chosen. At the time of this writing, solid state microwave generators in the 1–3 GHz range are expensive. Therefore, a conventional magnetron of the type commonly used in microwave ovens is utilized as the generator. It should be appreciated, however, that any other suitable microwave power source could be substituted in its place, and that the explained concepts may be applied at other frequencies like about 434 MHz, 915 MHz or 5.8 GHz (ISM band).

A frequent concern in the management of microwave energy is impedance matching of the various transmission line components with that of the power source. An impedance mismatch will reflect some portion of the incident power resulting in reduced energy transmission and increased losses, typically manifested as heat generation due to line or wave guide attenuation. Accordingly, it is desirable to match the impedance of the transmission line 28 with the incident power of the power source, which is typically on the order of fifty (50) ohms.

The transmission line 28 is therefore preferably provided by a conventional fifty (50) ohm coaxial design suitable for the transmission of microwave energy at frequencies in the range of about 400 to about 6000 megahertz. As shown in FIGS. 2 and 3, the coaxial transmission line 28 includes an inner conductor 31 and a concentric outer conductor 32 separated by a dielectric material medium 33. The inner conductor 31 is preferably provided by a solid metallic material core surrounded by a flexible semi-rigid dielectric material medium 33. The outer conductor 32 preferably includes a braided sleeve of metallic wires surrounding the inner conductor 31 to provide shielding and good flexibility thereof. However, when the biopsy needle is relatively straight, the outer conductor may be composed of a solid metallic tube material which substantially increases the penetration characteristics thereof.

Additionally, this transmission line 28 must be sufficiently flexible to accommodate normal operational use and storage thereof, yet be sufficiently rigid to prevent buckling of the line during penetrative manipulation of the antenna device 30 into the tumorous bio-tissue. Moreover, as will be described in greater detail below, this transmission line combination must be of a diameter sufficiently small to enable slideable insertion of at least the dielectric material medium 33 and the inner conductor 31 through the insert passage 26 of the needle shaft 35.

To achieve the above-indicated properties from a relatively small diameter ablation catheter while still maintaining the desired transmission properties (e.g., the impedance) for the electromagnetic field through the transmission line, the size and materials of the inner conductor 31, as well as the size, shape and material of the dielectric material medium must be carefully selected. Each of these variables of the transmission line, together with other factors related to the antenna device, may be used to adjust the impedance and energy transmission characteristics of the antenna device. Such preferable dielectric materials include TEFLON® or silicon, while the inner and outer conductors are preferably composed of copper or silver. Other factors to consider are the hardness or malleability of metallic material composing the inner conductor 31.

The impedance of the transmission line, for example, may be determined by the equation:

$$Z_O = (60 - LN^{(b/a)})/\sqrt{\in_r}$$

where "b" is the diameter of the dielectric material medium, "a" is the diameter of the inner conductor and $\in_r$ is the dielectric constant of the dielectric material medium. Therefore, the size of the inner conductor, the cross-sectional shape and dielectric properties of the surrounding dielectric medium are important factors in calculating the line impedance. For instance, in a fifty (50) ohm transmission line having a dielectric material medium of TEFLON®, the b/a ratio is equivalent to about 3.33, where "b" is the diameter of a cylindrical dielectric material medium and "a" is the diameter of its inner conductor. It will be understood, however, that the application of other microwave power supplies having an output impedance other than fifty (50) ohms would likely require a different transmission line for an impedance match.

In the preferred embodiment and as shown in FIG. 2, the antenna device 30 is provided by a monopole-type antenna which radiates a cylindrical electromagnetic field pattern consistent with the length thereof. This design is preferably formed by removing the outer conductor 32 along a portion of the transmission line 28. This exposed portion of the dielectric material medium 33 and the inner conductor 31 embedded therein define the antenna device 30 which enables the electromagnetic field to be radiated substantially radially perpendicular to the inner conductor 31. In this antenna arrangement, therefore, the antenna device 30 is integrally formed with the transmission line 28. Since the composition, the cross-sectional dimensions, and the electrical properties between the antenna device 30 and the transmission line 28 are substantially the same, there is very little impedance variation at the juncture or interface therebetween. Accordingly, the resulting power reflection caused at this interface is also substantially small which optimizes the energy coupling between the transmission line and the targeted tissues.

It will be appreciated, however, that the antenna device may be provided by other configurations as well. For example, the antenna device 30 may be helical or in the form of a coil, i.e. an antenna coil, which is made from any suitable material, such as spring steel, beryllium copper, or silver-plated copper. In other embodiments, the antenna device 30 may be wound from the inner conductor of the transmission line itself. In any of these alternative design choices, the antenna device must be dimensioned for sliding receipt in the needle shaft. Moreover, the antenna together with the interposed dielectric material medium must provide sufficient rigidity to the antenna structure to enable penetration into the bio-tissue during advancement past the needle distal penetration end 23. It will further be understood that these added variables will likely increase the power reflection at the antenna device/transmission line juncture.

Referring now to FIGS. 3A and 3B, the preferred embodiment of the present invention is illustrated wherein the transmission line 28 is appropriately sized such that only the dielectric material medium 33 and the inner conductor 31 are slideably received in the insert passage 26 of the needle shaft 35 during axial advancement of the antenna device therethrough and into the targeted bio-tissue 25. This arrangement is advantageous since, while maintaining the desired diametric ratio (b/a) of about 3.33 between the dielectric material medium 33 and the inner conductor 31, the diameters of the inner conductor 31 and the dielectric material medium 33 can be maximized relative the insert passage 26. The larger diameters, consequently, facilitate axial penetration into the bio-tissue due to the increased lateral and axial rigidity without compromising the impedance matching of about fifty (50) ohms.

In this arrangement, however, the antenna device 30 initially extends the full length of the exposed dielectric medium material 33 where the outer conductor 32 has been removed. The potential length of the antenna device 30, as shown in FIG. 3A, may therefore extend through the insert passage 26 and subject the needle shaft 35 to microwaves radiating from the exposed dielectric material medium 33 (i.e., the antenna device 30). Consequently, the metallic needle shaft 35 may be adversely heated during microwave generation by the antenna device 30.

To prevent adverse heating of the metallic biopsy needle 21, this embodiment of the microwave ablation assembly 20 adapts the metallic biopsy needle to operate as a conductive replacement for the outer conductor 32. Although the outer conductor 32 of the transmission line 28 has been removed to enable sliding receipt of the exposed dielectric material medium 33 and the inner conductor 31 in the insert passage 26, the tubular needle shaft 35 conductively functions as a shield for the transmission line 28 from the access opening 36 to the distal penetration opening 37 of the biopsy needle 21.

As best viewed in FIG. 3B, this shielding effect commences when the outer conductor 32 of the transmission line 28 and the metallic biopsy needle 21 are in conductive communication with one another. The outer conductor 32 must therefore be in conductive communication with the metallic needle shaft 35 at least when the antenna device 30 is generating microwaves. Once the electrical conduction is attained, the tubular needle shaft contains and shields the electromagnetic field in the same manner as the outer conductor.

In this preferred embodiment, a contact member 43 at the distal end of the outer conductor 32 is adapted to electrically contact a portion of the metallic biopsy needle 21 when the antenna device 30 is fully extended through the needle shaft 35 and into the targeted bio-tissue 25. Thus, the contact member 43 not only operates to electrically contact the biopsy needle for shielding of the exposed transmission line therein, but further functions as a stop device to limit the antenna device 30 penetration into the bio-tissue. This contact member may be provided by a connector or the like having a transverse-cross sectional dimension adapted to limit insertion into the insert passage 26. Preferably, the size dimension is merely larger than that of the access opening 36 into the insert passage 26

To assure an appropriate electrical contact between the contact member 43 and the biopsy needle 21, a coaxial connector could be used. In other configurations, the electrical contact may be performed through contact with the connector member 38 of the biopsy needle, such as shown in FIG. 5 to be discussed.

The selected length of the antenna device 30 in the configuration of FIG. 3B is measured from the center of the distal penetration opening 37 to the distal end of the antenna device 30. This length is also essentially equivalent to the length of the penetration into the bio-tissue, and may vary in accordance with the needs of a particular system. Several important factors that will dictate the antenna length, however, include the desired length of the lesion or ablation, the antenna configuration, the inner conductor diameter, the frequency of the electromagnetic energy, the desired field strength and the impedance match within the tissue (above-discussed). Another important consideration which is antenna length dependent is the desire to substantially reduce or eliminate electromagnetic radiance of the distal end of the transmission line 28 by feeding the antenna device 30 at its resonance frequency to better define the electromagnetic field along the inner conductor 31.

Such tuning of the antenna device 30 is preferably performed by adjusting its length so that the resonance frequency of the radiative structure is in the range of about 915 MHz or 2.45 GHz, for example. Consequently, the energy delivery efficiency of the antenna device 30 is increased, while the reflected microwave power is decreased which in turn reduces the operating temperature of the transmission line. Moreover, the radiated electromagnetic field is substantially constrained from the proximal end to the distal end of the antenna. Thus, the field extends substantially radially perpendicularly to the antenna and is fairly well constrained to the length of the antenna itself regardless of the power used. This arrangement serves to provide better control during ablation. Instruments having specified ablation characteristics can be fabricated by building instruments with different length antennas. For example, in microwave coagulonecrotic therapy applications for Hepatocellular Carcinoma (HCC) tumors, the monopole antenna may have an inner conductor diameter of about 0.013 inch, a dielectric material medium diameter of about 0.032, and a length in the range of approximately 10.0 mm to 25.0 mm.

Turning now to FIG. 4, an alternative embodiment to the present invention microwave ablation assembly 20 is illustrated wherein the complete transverse cross-sectional dimension of the transmission line 28, including the outer conductor 32, is appropriately sized for sliding receipt in the insert passage 26 of the needle shaft 35. Accordingly, once the biopsy needle is properly positioned, the integral antenna device 30 and the transmission line 28 can be axially advanced through the insert passage to position the antenna device 30 through the distal penetration opening 37 and into the targeted bio-tissue 25.

One of the primary advantages of this microwave ablation configuration is that the portion of the transmission line 28 slideably extending through the needle shaft 35 is already shielded, unlike the embodiment of FIGS. 3A and 3B. Thus, since the transmission line 28 does not require the outer conductor 32 to be removed to enable axial advancement through the insert passage 26, the potential problem with heating the biopsy needle 21 during microwave generation is no longer a concern. Moreover, since the biopsy needle 21 is not utilized to provide shielding for the transmission line 28, the needle shaft need not be conductive nor does an electrical connection need to be formed between the needle shaft and the outer conductor 32 of the transmission line 28. Finally, while the length of the antenna device 30 is subject to the same factors above-indicated, the outer conductor 32 does not pose a limitation to the insertion of the transmission line 28 into the insert passage. Thus, the position of the antenna device 30 past the distal penetration end 23 of the biopsy needle 21 is more adjustable, as shown in FIG. 4.

In accordance with the preferred diametric ratio (b/a) between the dielectric material medium 33 and the inner conductor 31 (e.g., about 3.33), the diameter of the inner conductor 31 must be smaller than that of the embodiment of FIGS. 3A and 3B. Depending upon the material compositions and hardness values of the components of the antenna device 30 and transmission line 28 can be carefully selected to provide the sufficient lateral and axial rigidity to enable axial penetration into the bio-tissue.

To further facilitate lateral and axial stiffness, for example, longitudinally extending stiffeners or the like (not shown) may be applied internally or externally to the transmission line 28 at the strategic locations therealong. These supports would stiffen the transmission line 28 at locations where manipulation of the transmission line is to occur, outside of the connector member 38, to facilitate axial advancement of the antenna device past the distal penetration end 23. Such stiffeners should be positioned so as not to interfere with insertion of the transmission line into the insert passage 26 of the needle shaft, yet be positioned to facilitate penetration of the antenna device into the targeted bio-tissue 25.

As shown in FIG. 5, an alternative to the embodiment of FIGS. 3A and 3B is illustrated having an outer conductor 32 providing a bore 45 formed for sliding receipt of the dielectric material medium 33 and the inner conductor 31 therein. Thus, the outer conductor 32 is in the form of a conductive sleeve electrically connected to the biopsy needle. To advance the antenna device 30, the exposed dielectric material medium and inner conductor combination are slideably positioned through the bore 45 of the conductive sleeve 32 and into the access opening 36 of the insert passage 26. Therefore, the tolerance between the inner surface of the conductive sleeve 32 defining bore 45 and the outer surface of the dielectric material medium 33 only need be sufficient to enable sliding receipt therebetween. Axial advancement continues until the distal end of the antenna device extends past the distal penetration end 23 of the needle shaft to a selected antenna length.

Similar to the embodiment of FIG. 3, the metallic biopsy needle 21 and conductive sleeve cooperate to contain and shield the electromagnetic field within the transmission line 28. Once the exposed dielectric material medium 33 extends past the needle shaft, the shielding is removed and the antenna device 30 is formed to ablate the targeted bio-tissue 25. Accordingly, the length of the antenna is determined and adjusted by the extension from the distal penetration opening 37.

Figure 6:
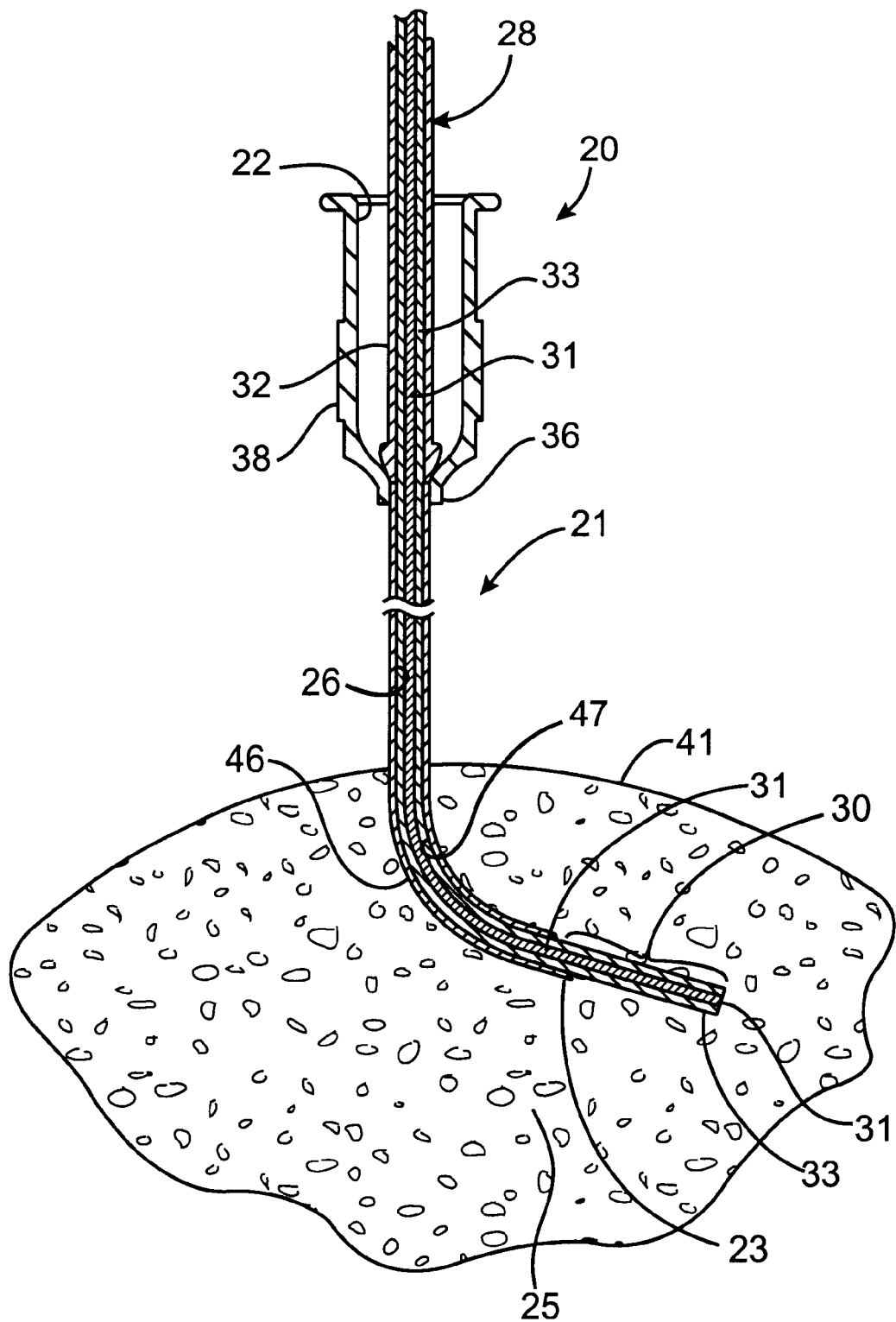
FIG. 6 is an enlarged side elevation view, in cross-section, of an alternative embodiment of the microwave ablation instrument assembly of FIG. 2 having a curved biopsy needle.

In the preferred configuration of this embodiment, the contact member 43 is provided by a conductive plug or the like conductively positioned between the connector member 38 of the biopsy needle 21 and the conductive sleeve. It will be appreciated, however, that any type of conductive contact may be made. Referring now to FIG. 6, an alternative embodiment of the present invention is illustrated wherein the needle shaft 35 of the biopsy needle 21 includes a curved section 46 which redirects the position of the antenna device 30 in a manner skewed from the longitudinal axis of the biopsy needle. As the distal end of the antenna device 30 contacts the curved wall 47 of the insert passage 26, the antenna device 30 is urged toward the distal penetration opening 37 and into the bio-tissue. Hence, the TEFLON® dielectric material medium is particularly suitable due in-part to its flexible, yet supportive, properties. It will be appreciated that this curved concept may be applied to any of the other embodiments as well.

In another aspect of the present invention, a method for ablating bio-tissue is provided including introducing an elongated probe 21 into the bio-tissue 25 to a predetermined depth. The probe defining a passage 26 extending therethrough from a proximal access end 22 to an opposite distal penetration end 23 thereof. The method further includes introducing into the passage 26 an elongated microwave ablation device 27 having a distal antenna 30 coupled to a transmission line 28 which in turn is coupled to a microwave energy source at a proximal end thereof. In accordance with the present invention, the method includes positioning the distal antenna 30 at least at the probe distal penetration end 23; and generating an electric field at the distal antenna 30 which is sufficiently strong to cause ablation of the bio-tissue within the electric field.

The introducing an elongated probe occurrence includes piercing the opposite distal penetration end 23 thereof into the bio-tissue 25 percutaneously. After the piercing and before the introducing into the passage 26, the method may include removing a specimen of bio-tissue through the biopsy needle.

In another embodiment of the present invention, the method includes removing a portion of the outer conductor 32 proximate a distal penetration end 23 of the transmission line 28 to expose a portion of the dielectric material medium 33 to from the antenna device 30. The method further includes electrically connecting the outer conductor to the biopsy needle 21 causing the same to function as a portion of the transmission line 28 and antenna device 30. This electrical connecting includes contacting the outer conductor 32 with the biopsy needle 21 during the advancing of the distal antenna 30 into the insert passage 26.

The introducing into the passage 26 may include inserting the distal antenna 30 and the transmission line 28, as a single unit, through an access opening 36 at the proximal access end 22 of the probe 21 and into the passage 26 toward the distal penetration end 23 thereof. The positioning the distal antenna may include advancing the distal antenna 30 through the passage 26 to a position beyond the penetration end 23 and further into the bio-tissue 25.

The inserting may further include inserting the distal antenna 30, the inner conductor 31, the dielectric material medium 33 and the outer conductor 32 into the insert passage of the biopsy needle 21 as a single unit.

Further, the electrically connecting event of the present invention may include precoupling a conductive sleeve 32 to the elongated probe 21 prior to piercing, and the introducing into the passage 26 event further includes slideably inserting the inner conductor 31 and the dielectric material medium 33 as a unit into the conductive sleeve 32.

In another method of the present invention for percutaneously ablating bio-tissue in a body cavity includes percutaneously piercing a penetration end 23 of a biopsy needle 21 into the bio-tissue 25 to a predetermined depth from outside the body cavity 40, the probe defining an insert passage 26 extending therethrough from an opposite access end 22 to the penetration end 23 thereof. The method then includes inserting into the insert passage 26 an elongated microwave ablation device 27 having a distal antenna 30 coupled to a transmission line 28 which in turn is coupled to a microwave energy source at a proximal end thereof. The next event includes advancing the distal antenna 30 through the insert passage 26 to a position beyond the penetration end 23 and further into the bio-tissue 25; and generating an electric field at the distal antenna 30 which is sufficiently strong to cause ablation of the bio-tissue 25 within the electric field.

What is claimed is:

1. A microwave ablation assembly comprising:
an elongated probe having a penetration end adapted to penetrate into bio-tissue and an opposite access end, said probe defining an insert passage extending therethrough from the access end to the penetration end thereof;

a coaxial transmission line including an inner conductor and an outer conductor separated by a dielectric material medium, and having a proximal end coupled to a microwave energy source; and an antenna device for generating an electric field sufficiently strong to cause tissue ablation, said antenna device being integrally formed by said inner conductor and said dielectric material medium extending beyond a distal portion of said outer conductor, said dielectric material medium having a transverse cross-sectional dimension sized for sliding receipt through said insert passage, while said elongated probe is positioned in the bio-tissue, to a position advancing said antenna device beyond said penetration end and further into said bio-tissue, and said dielectric material medium further being sized to prevent said outer conductor from extending through said insert passage.

2. A microwave ablation assembly as defined in claim 1, wherein said elongated probe is a conductor.

3. A microwave ablation assembly as defined in claim 1, wherein a distal end of said outer conductor is adapted to electrically couple to said elongated probe proximate the access end such that said probe functions as a shield for said transmission line.

4. A microwave ablation assembly as defined in claim 3, wherein the length of antenna device is a function of the frequency of said electric field.

5. A microwave ablation assembly as defined in claim 1, wherein said elongated probe is metallic, and a distal end of said outer conductor is adapted to electrically couple to said elongated probe proximate the access end such that said probe functions as a shield for said transmission line.

6. A microwave ablation assembly as defined in claim 1, wherein the length of antenna device is a function of the frequency of said electric field.

7. A microwave ablation assembly as defined in claim 1, wherein said coaxial transmission line is suitable for transmission of microwave energy at frequencies in the range of about 400 to about 6000 megahertz, and the diameter of said inner connector in combination with said dielectric material medium is sufficient to enable penetration into said bio-tissue.

8. A microwave ablation assembly as defined in claim 1, wherein said coaxial transmission line is suitable for transmission of microwave energy at frequencies in the range of about 400 to about 6000 megahertz, and the diameter of said inner connector in combination with said dielectric material medium is sufficient to enable penetration into said bio-tissue.

9. A microwave ablation assembly for insertion through an insert passage of an elongated metallic biopsy needle having a penetration end adapted to penetrate into bio-tissue, said insert passage extending from an access opening to an insert opening at the penetration end, said ablation assembly comprising:

a coaxial transmission line including an inner conductor and an outer conductor separated by a dielectric material medium, and having a proximal end thereof coupled to a microwave energy source; and an antenna device for generating an electric field sufficiently strong to cause tissue ablation, said antenna device being integrally formed by said inner conductor and said dielectric material medium extending beyond a distal portion of said outer conductor, wherein said dielectric material medium has a transverse cross-sectional dimension adapted for sliding receipt through said insert passage while said biopsy needle is positioned in the bio-tissue, and to a position advancing said antenna beyond said insert opening and further into said bio-tissue, and wherein said outer conductor has a transverse cross section dimension sized to prevent passage thereof through said access opening and into said insert passage in a manner contacting said biopsy needle to limit the advancement of said antenna beyond said insert opening, and to electrically couple to said biopsy needle such that said needle functions as a shield for the dielectric material medium and said inner conductor in said insert passage.

10. A microwave ablation assembly as defined in claim 9, wherein the length of antenna device is a function of the frequency of said electric field.

11. A microwave ablation assembly as defined in claim 9, wherein a distal end of said outer conductor is adapted to electrically couple to said biopsy needle proximate the access opening.

12. A microwave ablation assembly as defined in claim 9, wherein the diameter of said inner connector in combination with said dielectric material medium is sufficient to enable penetration into said bio-tissue.

13. A method for ablating bio-tissue comprising:

piercing an elongated probe into the bio-tissue percutaneously to a predetermined depth, said probe defining a passage extending therethrough from a proximal access end to an opposite distal end thereof;

removing a specimen of bio-tissue through said biopsy needle;

introducing into the passage an elongated microwave ablation device having a distal antenna coupled to a transmission line which in turn is coupled to a microwave energy source at a proximal end thereof;

positioning the distal antenna at least at the probe distal end; and generating an electric field at the distal antenna which is sufficiently strong to cause ablation of the bio-tissue within the electric field.

14. The method according to claim 13, wherein said opposite distal end is needle-shaped.

15. The method according to claim 13, wherein, said positioning the distal antenna includes advancing the distal antenna through said passage to a position beyond said penetration end and further into said bio-tissue.

16. The method according to claim 13, further including:

said transmission line is coaxial including an inner conductor and an outer conductor separated by a dielectric material medium therebetween, and further including:

removing a portion of said outer conductor proximate a distal end of said transmission line to expose a portion of the dielectric material medium to form said antenna device.

17. The method according to claim 16, wherein, said elongated probe is electrically conductive, and further including:
electrically connecting said outer conductor to said elongated probe causing the same to function as the transmission line and the antenna device.

18. The method according to claim 13, wherein, said antenna device is sufficiently rigid to enable further penetration into the bio-tissue during the advancing the distal antenna.

19. The method according to claim 18, wherein, said transmission line is coaxial having an inner conductor and an outer conductor separated by a dielectric material medium such that the diameter of said inner connector in combination with said dielectric material medium provides the sufficient rigidity.

20. A method of percutaneously ablating bio-tissue in a body cavity comprising:
percutaneously piercing a penetration end of a biopsy needle into the bio-tissue to a predetermined depth from outside the body cavity, said biopsy needle defining an insert passage extending therethrough from an opposite access end to the penetration end thereof;
removing a specimen of bio-tissue through said biopsy needle;
inserting into the insert passage an elongated microwave ablation device having a distal antenna coupled to a transmission line which in turn is coupled to a microwave energy source at a proximal end thereof;
advancing the distal antenna through said insert passage to a position beyond said penetration end and further into said bio-tissue; and
generating an electric field at the distal antenna which is sufficiently strong to cause ablation of the bio-tissue within the electric field.

21. The method according to claim 20, wherein said transmission line is coaxial including an inner conductor and an outer conductor separated by a dielectric material medium therebetween, and further including:
removing a portion of said outer conductor proximate a distal end of said transmission line to expose a portion of the dielectric material medium to form said antenna device.

22. The method according to claim 21, wherein said biopsy needle is metallic, and further including:
electrically connecting said outer conductor to said biopsy needle causing the same to function as a portion of the transmission line and antenna device.

23. The method according to claim 22, wherein said electrically connecting includes contacting the outer conductor with the biopsy needle during the advancing of the distal antenna into the insert passage.

24. The method according to claim 20, wherein said transmission line is a coaxial transmission line suitable for transmission of microwave energy at frequencies in the range of about 400 to about 6000 megahertz, and includes an inner conductor and an outer conductor separated by a dielectric material medium therebetween, and further including:
removing a portion of said outer conductor proximate a distal end of said transmission line to expose a portion of the dielectric material medium to form said antenna device.

25. The method according to claim 24, wherein, said biopsy needle is electrically conductive, and further including:
electrically connecting said outer conductor to said elongated probe causing the same to function as the transmission line and the antenna device.

26. The method according to claim 25, wherein, said antenna device is sufficiently rigid to enable further penetration into the bio-tissue during the advancing the distal antenna.

27. The method according to claim 26, wherein, said transmission line is coaxial having an inner conductor and an outer conductor separated by a dielectric material medium such that the diameter of said inner connector in combination with said dielectric material medium provides the sufficient rigidity.

28. A microwave ablation assembly comprising:
a conductive, elongated probe having a penetration end adapted to penetrate into bio-tissue and an opposite access end, said probe defining an insert passage extending therethrough from the access end to the penetration end thereof;
a coaxial transmission line including an inner conductor and an outer conductor separated by a dielectric material medium, and having a proximal end coupled to a microwave energy source; and
an antenna device for generating an electric field sufficiently strong to cause tissue ablation, said antenna device being integrally formed by said inner conductor and said dielectric material medium extending beyond a distal portion of said outer conductor, said dielectric material medium having a transverse cross-sectional dimension sized for sliding receipt through said insert passage, while said elongated probe is positioned in the bio-tissue, to a position advancing said antenna device beyond said penetration end and further into said bio-tissue;
wherein said distal portion of said outer conductor is adapted to contact and to electrically couple to said biopsy needle such that said needle functions as a shield for the dielectric material medium and said inner conductor in said insert passage.

29. A microwave ablation assembly as defined in claim 28, wherein the length of antenna device is a function of the frequency of said electric field.

30. A microwave ablation assembly as defined in claim 28, wherein said elongated probe is metallic.

31. A method of percutaneously ablating bio-tissue in a body cavity comprising:
providing a coaxial transmission line having a proximal end coupled to a microwave energy source, and having an inner conductor and an outer conductor separated by a dielectric material medium therebetween, a portion of said outer conductor being removed proximate a distal end of said transmission line to expose a portion of the dielectric material medium to form a distal said antenna device;
percutaneously piercing a penetration end of a conductive biopsy needle into the bio-tissue to a predetermined depth from outside the body cavity, said biopsy needle defining an insert passage extending therethrough from an opposite access end to the penetration end thereof;
inserting into the insert passage the distal antenna;
advancing the distal antenna through said insert passage to a position beyond said penetration end and further into said bio-tissue;

electrically connecting said outer conductor to said elongated probe causing the same to function as the transmission line and the antenna device; and generating an electric field at the distal antenna which is sufficiently strong to cause ablation of the bio-tissue within the electric field.

32. The method according to claim 31, further including:

after the piercing and before the inserting, removing a specimen of bio-tissue through said biopsy needle.

33. The method according to claim 31, wherein said electrically connecting includes contacting the outer conductor with the biopsy needle during the advancing of the distal antenna into the insert passage.

34. The method according to claim 31, wherein, said antenna device is sufficiently rigid to enable further penetration into the bio-tissue during the advancing the distal antenna.

35. A method for ablating bio-tissue comprising:

providing a coaxial transmission line having a proximal end coupled to a microwave energy source, and having an inner conductor and an outer conductor separated by a dielectric material medium therebetween, a portion of said outer conductor being removed proximate a distal end of said transmission line to expose a portion of the dielectric material medium to form a distal said antenna device;

introducing a conductive, elongated probe into the bio-tissue to a predetermined depth, said probe defining a passage extending therethrough from a proximal access end to an opposite distal end thereof;

introducing into the passage the distal antenna;

positioning the distal antenna at least at the probe distal end;

electrically connecting said outer conductor to said elongated probe causing the same to function as the transmission line and the antenna device; and generating an electric field at the distal antenna which is sufficiently strong to cause ablation of the bio-tissue within the electric field.

36. The method according to claim 35, wherein said introducing an elongated probe includes piercing the opposite distal end thereof into the bio-tissue percutaneously.

37. The method according to claim 36, wherein said opposite distal end is needle-shaped.

38. The method according to claim 37, wherein said elongated probe is a biopsy needle, and further including, after the piercing and before the introducing into the passage, removing a specimen of bio-tissue through said biopsy needle.

39. The method according to claim 35, wherein said electrically connecting includes contacting the outer conductor with the probe during the advancing of the distal antenna into the insert passage.

40. The method according to claim 35, wherein, said positioning the distal antenna includes advancing the distal antenna through said passage to a position beyond said penetration end and further into said bio-tissue.

41. The method according to claim 35, wherein, said antenna device is sufficiently rigid to enable further penetration into the bio-tissue during the advancing the distal antenna.

* * * * *